(12) United States Patent
Mattar et al.

(10) Patent No.: US 7,117,717 B2
(45) Date of Patent: Oct. 10, 2006

(54) DENSITOMETER WITH PULSING PRESSURE

(75) Inventors: Wade M. Mattar, Wrentham, MA (US); James H. Vignos, Needham Heights, MA (US)

(73) Assignee: Invensys Systems, Inc., Foxboro, MA (US)

( * ) Notice: Subject to any disclaimer, the term of this patent is extended or adjusted under 35 U.S.C. 154(b) by 0 days.

(21) Appl. No.: 11/009,511

(22) Filed: Dec. 13, 2004

(65) Prior Publication Data

US 2005/0138993 A1   Jun. 30, 2005

Related U.S. Application Data

(60) Provisional application No. 60/528,702, filed on Dec. 12, 2003.

(51) Int. Cl.
  G01N 9/00    (2006.01)
  G01N 7/00    (2006.01)
  G01N 29/00   (2006.01)
(52) U.S. Cl. .................... 73/19.03; 73/32 A; 73/61.47; 73/61.78; 73/61.79
(58) Field of Classification Search ............... 73/19.01, 73/19.03, 19.05, 32 A, 61.47, 61.78, 61.79
  See application file for complete search history.

(56) References Cited

U.S. PATENT DOCUMENTS 5,224,372 A * 7/1993 Kolpak ...................... 73/19.03
6,496,781 B1   12/2002 Chen et al.
6,766,680 B1 * 7/2004 Chen et al. ................ 73/19.05
2004/0206157 A1 * 10/2004 Chen et al. ................ 73/19.05

OTHER PUBLICATIONS

Copy of International Search Report mailed Feb. 24, 2006 for PCT/US04/41432, filed Dec. 13, 2004.
Copy of Written Opinion mailed Feb. 24, 2006 for PCT/US04/41432, filed Dec. 13, 2004.

* cited by examiner

Primary Examiner—Hezron Williams
Assistant Examiner—John C Hanley
(74) Attorney, Agent, or Firm—Fish & Richardson P.C.

(57) ABSTRACT

Techniques for measuring a density of a liquid within a fluid that includes both a liquid and a gas are described. A pressure of the fluid oscillates according to a time-varying function, which causes a density of the fluid also to oscillate according to the same time-varying function. A resulting pressure signal and density signal are analyzed to extract at least a first and second pressure value and at least a first and second density value, where the first pressure and density values occur at a first time, and the second pressure and density values occur at a second time. Then, the liquid density is calculated from the first and second pressure and density values. As a result, the liquid density may be calculated quickly and easily, with a minimum of effort on the part of an operator, and without requiring disruption of other measurement processes associated with the flowtube.

20 Claims, 5 Drawing Sheets

DENSITOMETER WITH PULSING PRESSURE

CLAIM OF PRIORITY

This application claims priority under 35 USC §119(e) to U.S. Patent Application Ser. No. 60/528,702, filed on Dec. 12, 2003, and titled "FLOWMETER WITH PULSING PRESSURE," the entire contents of which are hereby incorporated by reference.

TECHNICAL FIELD

This description relates to density measurements.

BACKGROUND

Flowmeters provide information about materials being transferred through a conduit. For example, mass flowmeters provide a measurement of the mass of material being transferred through a conduit. Similarly, density meters, or densitometers, provide a measurement of the density of material flowing through a conduit. Mass flowmeters also may provide a measurement of the density of the material.

For example, Coriolis-type mass flowmeters are based on the Coriolis effect, in which material flowing through a conduit becomes a radially-travelling mass that is affected by a Coriolis force and therefore experiences an acceleration. Many Coriolis-type mass flowmeters induce a Coriolis force by sinusoidally oscillating a conduit about a pivot axis orthogonal to the length of the conduit. In such mass flowmeters, the Coriolis reaction force experienced by the traveling fluid mass is transferred to the conduit itself and is manifested as a deflection or offset of the conduit in the direction of the Coriolis force vector in the plane of rotation.

SUMMARY

According to one general aspect, a pressure of a process fluid in a flowtube is varied according to a time-varying function, where the process fluid contains a liquid component and a gas component. Pressure values and density values of the process fluid that occur during the varying of the pressure are determined, and a liquid density of the liquid component is determined, based on the pressure values and the density values.

Implementations may include one or more of the following features. For example, a percentage of the gas component, by volume, within the process fluid and during the varying of the pressure may be determined, based on the pressure values and the density values.

In determining the pressure values and the density values, a first pressure value and a second pressure value of the process fluid may be determined at a first time and a second time, respectively, during the varying of the pressure, and a first density value and a second density value of the process fluid may be determined at the first time and the second time, respectively.

In this case, determining the liquid density may include calculating the liquid density using an equation:

$$D_{LIQ} = \frac{D_1}{\left(1 - \left[\frac{\left[1 - \left(\frac{D_1}{D_2}\right)\right]}{\left[1 - \left(\frac{P_1}{P_2}\right)\right]}\right]\right)}$$

where $D_{LIQ}$ is the liquid density, $D_1$ and $D_2$ are the first density value and the second density value, respectively, and $P_1$ and $P_2$ and are the first pressure value and the second pressure value, respectively.

Further, a percentage of the gas component, by volume, within the process fluid and during the varying of the pressure, based on the pressure values and the density values, may be determined using an equation:

$$VF = \frac{\left[1 - \left(\frac{D_1}{D_2}\right)\right]}{\left[1 - \left(\frac{P_1}{P_2}\right)\right]}$$

where VF is the percentage of the gas component, by volume, $D_1$ and $D_2$ are the first density value and the second density value, respectively, and $P_1$ and $P_2$ and are the first pressure value and the second pressure value, respectively.

Determining the pressure values and the density values may include measuring a density of the process fluid. Measuring the density of the process fluid may include measuring the density of the process fluid using a Coriolis flowmeter.

In varying the pressure of the process fluid, a pressure valve may be operated to establish a periodic, continuous oscillation of the pressure according to the time-varying function, such that the pressure values and the density values oscillate in accordance with the continuous oscillation. In this case, the determining of the pressure values and the density values may include determining amplitudes of oscillation of the pressure values and the density values, determining average values of the pressure values and the density values, and determining the pressure values and the density values, based on the amplitudes of oscillation and the average values.

The oscillation may have an associated frequency of oscillation, and the determining of the pressure values and the density values may include measuring the pressure values and the density values, using the frequency of oscillation. In this case, the frequency of oscillation may be small compared to an operating frequency associated with the flowtube, such that the frequency of oscillation substantially does not affect operating measurements of the flowtube.

The pressure values and the density values may be determined with respect to a single portion of the flowtube.

According to another general aspect, a system includes a pressure controller operable to control a variation in a pressure of a fluid within a flowtube in accordance with a time-varying function, the fluid including a gas component and a liquid component, a pressure sensor operable to determine pressure values associated with the fluid that occur during the variation of the pressure, a densitometer that is operable to determine density values associated with the fluid that occur during the variation of the pressure, and a liquid density determination system that is operable to determine a liquid density of the liquid component of the fluid, based on the pressure values and the density values.

Implementations may include one or more of the following features. For example, the system may include a void fraction determination system that is operable to determine a percentage of the gas component, by volume, within the fluid and during the variation of the pressure, based on the pressure values and the density values.

The pressure sensor may be operable to determine the pressure values by determining a first pressure value and a second pressure value of the fluid at a first time and a second time, respectively, during the variation of the pressure, and the densitometer may be operable to determine a first density value and a second density value of the fluid at the first time and the second time, respectively. The pressure controller may be operable to vary the pressure of the fluid by operating a pressure valve to establish a periodic, continuous oscillation of the pressure according to the time-varying function, such that the pressure values and the density values oscillate in accordance with the periodic, continuous oscillation.

According to another general aspect, a densitometer controller includes a pressure controller operable to control a variation in a pressure of a fluid within a flowtube in accordance with a time-varying function, the fluid including a gas component and a liquid component, a pressure determination system operable to communicate with a pressure sensor to determine pressure values associated with the fluid that occur during the variation of the pressure, a density determination system operable to communicate with a densitometer to determine density values associated with the fluid that occur during the variation of the pressure, and a liquid density determination system that is operable to determine a liquid density of the liquid component of the fluid, based on the pressure values and the density values.

Implementations may include one or more of the following features. For example, the densitometer controller may include a void fraction determination system that is operable to determine a percentage of the gas component, by volume, within the fluid and during the variation of the pressure, based on the pressure values and the density values.

The pressure determination system may be operable to determine the pressure values by receiving a pressure signal from the pressure sensor and determining a first pressure value and a second pressure value of the fluid at a first time and a second time, respectively, during the variation of the pressure, based on the pressure signal, and the density determination system may be operable to determine a first density value and a second density value of the fluid at the first time and the second time, respectively, based on a density signal received from the densitometer.

The pressure controller may be operable to vary the pressure of the fluid by operating a pressure valve to establish a periodic, continuous oscillation of the pressure according to the time-varying function, such that the pressure values and the density values oscillate in accordance with the periodic, continuous oscillation.

The details of one or more implementations are set forth in the accompanying drawings and the description below. Other features will be apparent from the description and drawings, and from the claims.

DETAILED DESCRIPTION

Types of flowmeters include digital flowmeters. For example, U.S. Pat. No. 6,311,136, which is hereby incorporated by reference, discloses the use of a digital flowmeter and related technology including signal processing and measurement techniques. Such digital flowmeters may be very precise in their measurements, with little or negligible noise, and may be capable of enabling a wide range of positive and negative gains at the driver circuitry for driving the conduit. Such digital flowmeters are thus advantageous in a variety of settings. For example, commonly-assigned U.S. Pat. No. 6,505,519, which is incorporated by reference, discloses the use of a wide gain range, and/or the use of negative gain, to prevent stalling and to more accurately exercise control of the flowtube, even during difficult conditions such as two-phase flow.

Analog flowmeters also exist. Although such analog flowmeters may be prone to typical shortcomings of analog circuitry, e.g., low precision and high noise measurements relative to digital flowmeters, they also may be compatible with the various techniques and implementations discussed herein. Thus, in the following discussion, the term "flowmeter" or "meter" is used to refer to any type of device and/or system in which a flowmeter system, such as, for example, a Coriolis flowmeter system uses various control systems and related elements to measure a mass flow, density, and/or other parameters of a material(s) moving through a flowtube or other conduit.

Figure 1A:
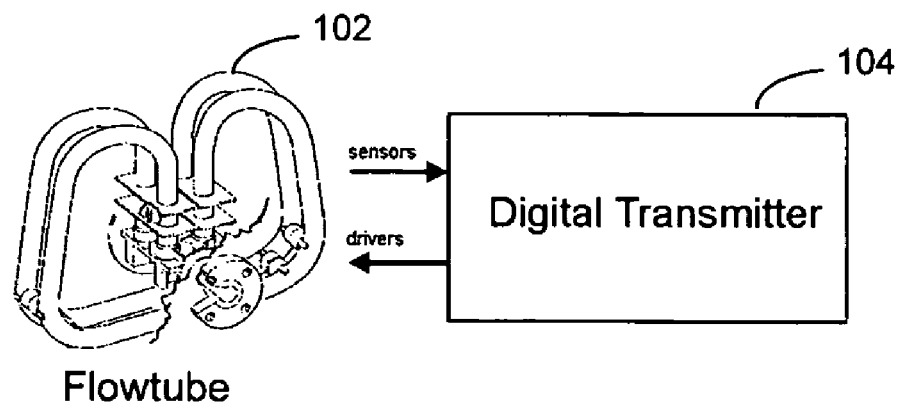
FIG 1A is an illustration of a flowmeter using a bent flowtube.

FIG. 1A is an illustration of a flowmeter using a bent flowtube 102. Specifically, the bent flowtube 102 may be used to measure one or more physical characteristics of, for example, a (traveling) fluid, such as, for example, density, as referred to above. In FIG. 1A, a digital transmitter 104 exchanges sensor and drive signals with the bent flowtube 102, so as to both sense an oscillation of the bent flowtube 102, and to drive the oscillation of the bent flowtube 102 accordingly. By quickly and accurately determining the sensor and drive signals, the digital transmitter 104, as referred to above, provides for fast and accurate operation of the bent flowtube 102. Examples of the transmitter 104 being used with a bent flowtube are provided in, for example, commonly-assigned U.S. Pat. No. 6,311,136.

Figure 1B:
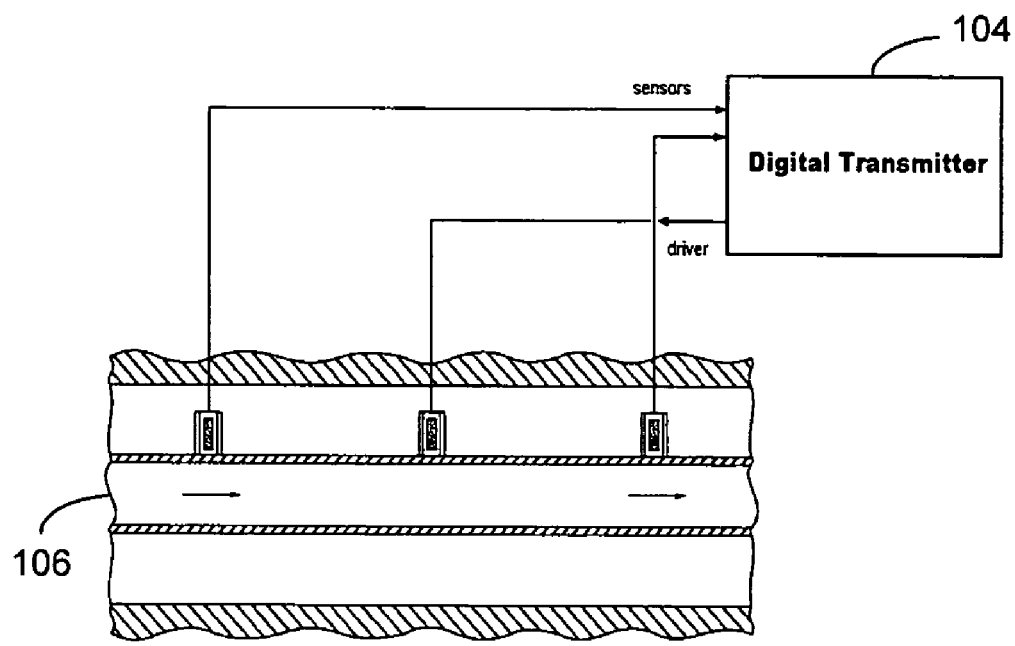
FIG 1B is an illustration of a flowmeter using a straight flowtube.

FIG. 1B is an illustration of a flowmeter using a straight flowtube 106. More specifically, in FIG. 1B, the straight flowtube 106 interacts with the digital transmitter 104. Such a straight flowtube operates similarly to the bent flowtube 102 on a conceptual level, and has various advantages/disadvantages relative to the bent flowtube 102. For example, the straight flowtube 106 may be easier to (completely) fill and empty than the bent flowtube 102, simply due to the geometry of its construction. In operation, the bent flowtube 102 may operate at a frequency of, for example, 50–110 Hz, while the straight flowtube 106 may operate at a frequency of, for example, 300–1,000 Hz.

Figure 2:
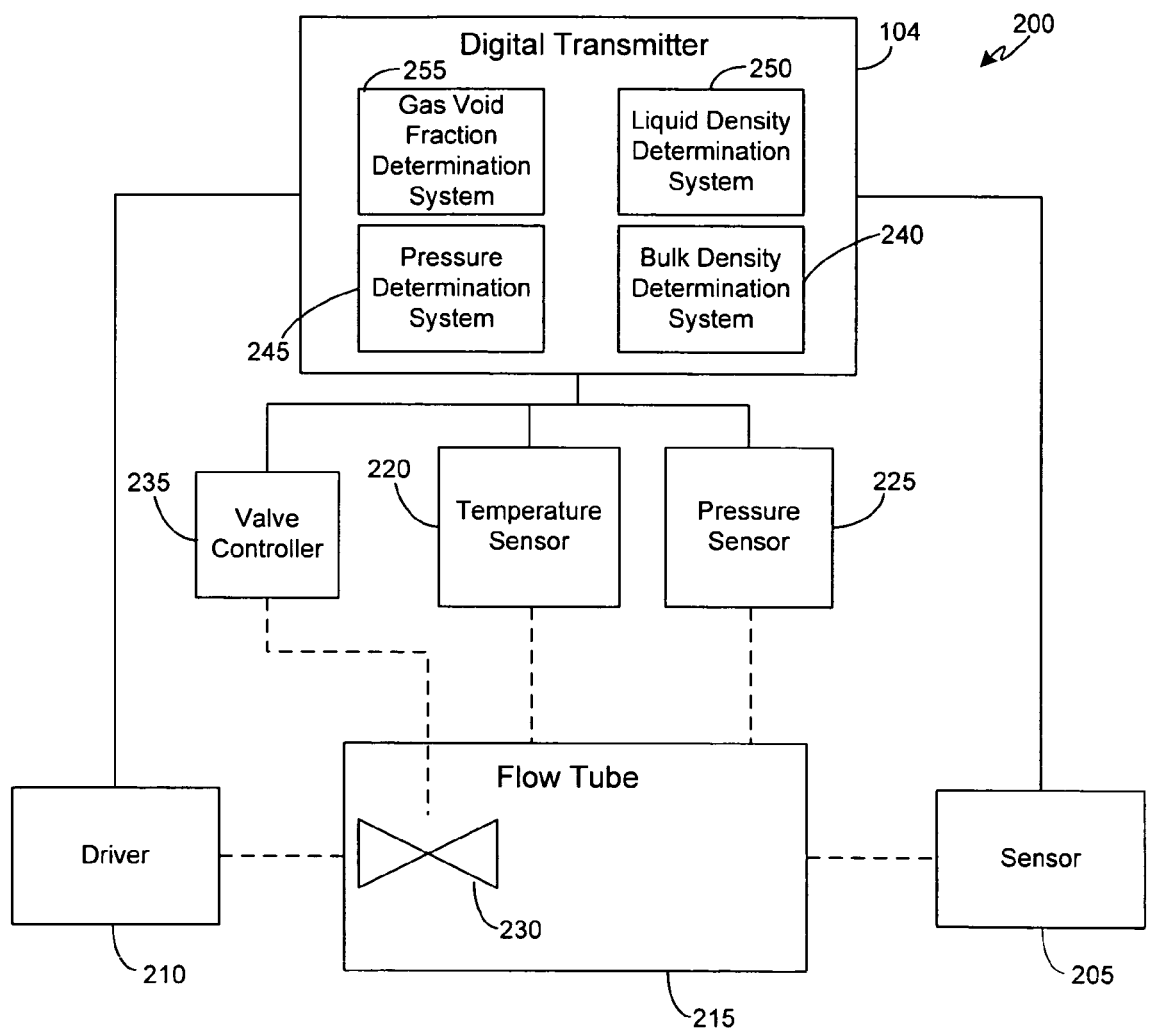
FIG. 2 is a block diagram of a flowmeter with pulsing pressure.

FIG. 2 is a block diagram of a flowmeter with pulsing pressure. In FIG. 2, a digital mass flowmeter 200 includes the digital transmitter 104, one or more motion sensors 205, one or more drivers 210, a flowtube 215 (which also may be referred to as a conduit, and which may represent either the bent flowtube 102, the straight flowtube 106, or some other type of flowtube), and a pressure sensor 220. The digital transmitter 104 may be implemented using one or more of, for example, a processor, a Digital Signal Processor (DSP), a field-programmable gate array (FPGA), an ASIC, other programmable logic or gate arrays, or programmable logic with a processor core.

The digital transmitter 104 generates a measurement of, for example, density and/or mass flow of a material flowing through the flowtube 215, based at least on signals received from the motion sensors 205. The digital transmitter 104 also controls the drivers 210 to induce motion in the flowtube 215. This motion is sensed by the motion sensors 205.

Density measurements of the material flowing through the flowtube are related to, for example, the frequency of the motion of the flowtube 215 that is induced in the flowtube 215 by a driving force supplied by the drivers 210, and/or to the temperature of the flowtube 215. Similarly, mass flow through the flowtube 215 is related to the phase and frequency of the motion of the flowtube 215, as well as to the temperature of the flowtube 215. The flowmeter 200 may be configured to measure only density, and to thereby operate as a densitometer.

The temperature in the flowtube 215, which is measured using the temperature sensor 220, affects certain properties of the flowtube, such as its stiffness and dimensions. Also in FIG. 2, a pressure sensor 225 is illustrated that is in communication with the transmitter 104, and is connected to the flowtube 215 so as to be operable to sense a pressure of a material flowing through the flowtube 215.

As referred to above, densitometers such as, for example, a coriolis flowmeter can determine the density of a process fluid in the flowtube 215. That is, an accurate density of the process fluid can typically be determined. In some situations, the process fluid is a binary mixture of two materials, such as, for example, oil and water. In such cases, also referred to as "two-phase flows," a relative percentage of each constituent may be determined using, for example, an algebraic sum or an algorithm relating density to composition.

In other situations, a two-phase flow may further involve a gas (e.g., air) mixed with the liquid(s). In such cases, because the gas is an additional component, it may be difficult either to determine the void fraction (gas content) and/or measure the density of the liquid phase density. Rather, a "bulk density," including both the liquid and gas within the fluid, is read by the meter.

In many cases, however, an operator of the meter 200 does not require this bulk density, and prefers information regarding just the liquid density (or mass flow rate of the liquid, or other determinable parameter), without any effect from the gas content. That is, in many situations, the gas content represents an undesired or unavoidable effect on a fluid flow measurement, the impact of which must be reduced or eliminated for the operator to obtain a desired measurement (e.g., a density of the liquid component).

In FIG. 2, a pressure drop may be created within the flowtube 215, using, for example, a valve 230. Using the valve 230, a pressure drop may be created in the process fluid within the flowtube 215 over a period of time, where the pressure drop is controlled by 104 and connected to the valve 230.

Specifically, the valve 230 is set into an oscillation by the valve controller 235, where the frequency of oscillation is slow relative to an operating frequency of the flowmeter (for example, the pressure oscillation frequency may be a factor of ten or less than the operating frequency of the flowmeter). This oscillating pressure is then sensed by the pressure sensor 225.

This oscillating pressure causes a corresponding oscillation of the volume of the gas phase within the process fluid, and, correspondingly, an oscillation of the density of the gas and the bulk density. Thus, within the transmitter 104, a bulk density determination system 240 and a pressure determination system 245 may be used to measure the bulk density and pressure, respectively, of the process flow.

By determining and comparing properties of the measured pressure and bulk density, techniques for which are discussed in more detail below, the liquid density of the liquid component may be determined by a liquid density determination system 250, and, additionally or alternatively, the gas void fraction (i.e., a percentage of gas within the fluid flow, by volume) may be determined by a gas void fraction determination system 255. In particular, the liquid density and/or gas void fraction may be determined during a time in which normal operations of the meter 200 are maintained. As a result, measurements of liquid density may be obtained during a first fluid flow, and, if a composition of the fluid flow changes (e.g., the relative percentages of gas/liquid are altered, and/or a new type of liquid or gas is included in place of a previous liquid or gas), the liquid density may rapidly and accurately be determined again.

As a result, for example, there is no need to halt operations of the flowmeter, or to siphon part of the fluid flow to a separate container or reservoir for a determination of liquid (gas-free) density (or gas void fraction), or to obtain an equilibrium state of the flowmeter before determining liquid density. Rather, operation of the flowmeter (including output of liquid densities, or output of other measurement parameters, if any, such as, for example, a mass flow rate of the fluid flow) may be maintained throughout a period of varying conditions of fluid flow, leading to an increased efficiency of use of the flowmeter. Moreover, the liquid density and/or gas void fraction measurement may be obtained by an operator with a minimum of time and effort.

Additionally, as will be apparent from the below discussion, only a single pressure sensor and density sensor are required to obtain the void fraction and/or liquid density. Therefore, an amount of sensor equipment needed, and an amount of space needed to use the equipment to obtain the void fraction and/or liquid density measurements, may be minimized.

Figure 3:
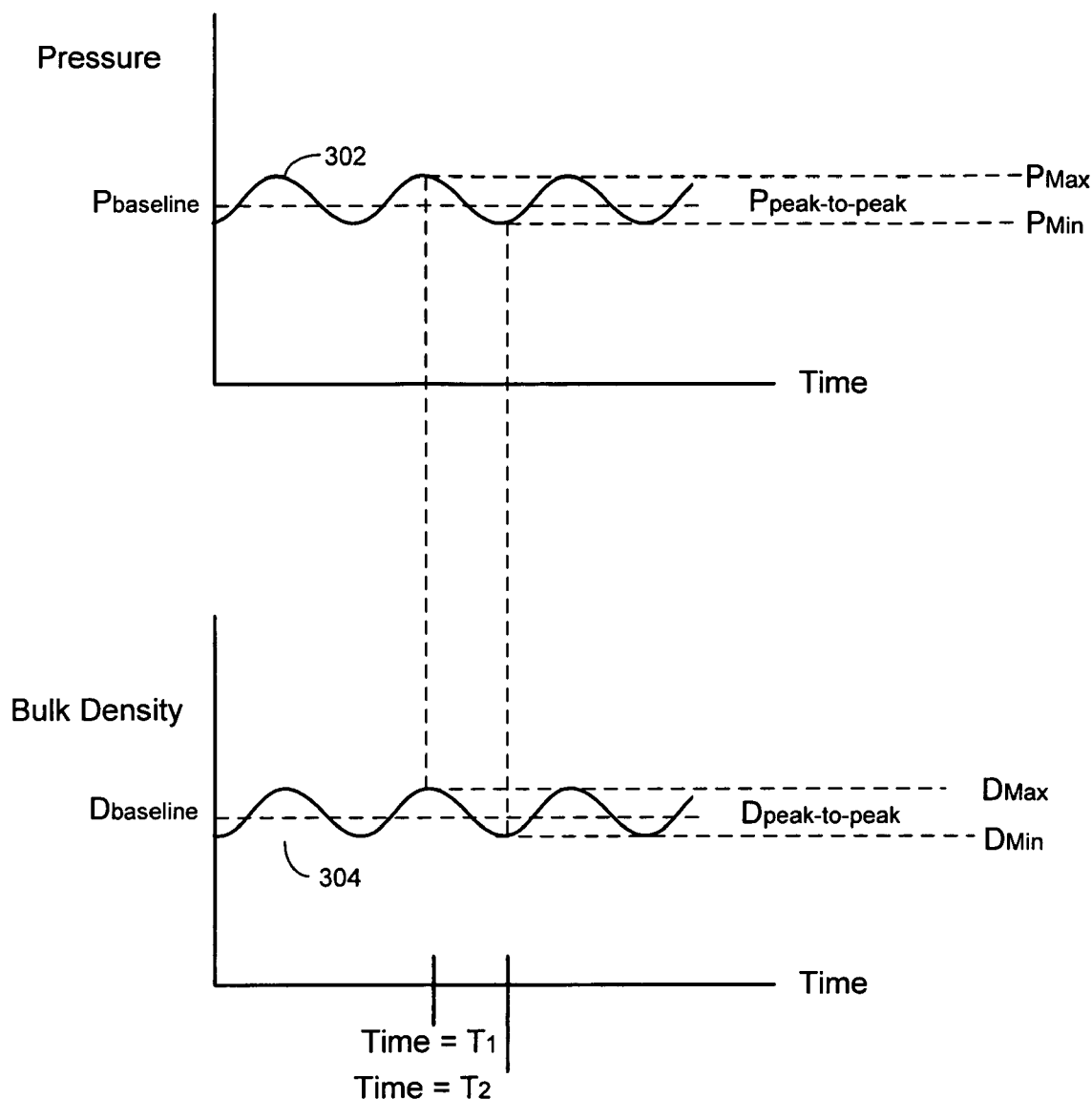
FIG. 3 is a pair of graphs illustrating pressure and density characteristics and measurements determined by the flowmeter of FIG. 2.

FIG. 3 is pair of graphs 300 illustrating pressure and density characteristics and measurements determined by the flowmeter 200 of FIG. 2. In FIG. 3, as above, it is assumed that a fluid flow occurs through the flowtube 215, where the fluid flow includes a fluid including both liquid and gas.

Using the pressure and density measurements, as obtained from the pressure determination system 245 (by way of the pressure sensor 255) and the bulk density determination system 240 (by way of the sensor(s) 205), respectively, the liquid density determination system 250 calculates a gas-free, liquid density of the liquid portion of the fluid flow. Additionally, or alternatively, the gas void fraction determination system 255 may calculate the gas void fraction of the fluid flow, using measurements from the pressure determination system 245 and the bulk density determination system 240.

More specifically, as shown in FIG. 3, the fluid flow through the flowtube 215 has a baseline value $P_{baseline}$ that represents a pressure experienced by the fluid flow, without any operation of the valve 230 and valve controller 235. As the valve 230 begins to operate, a time-varying, generally sinusoidal fluctuation of the pressure occurs about this baseline, as shown in a pressure signal 302 of FIG. 3, and having a peak-to-peak value defined as a difference between a maximum amplitude $P_{MAX}$ and a minimum amplitude $P_{MIN}$, as also shown with respect to the pressure signal 302.

As mentioned above, a frequency of the time-varying pressure oscillation is made to be small in frequency, relative to operating frequencies of the flowmeter 200. Exact values for a frequency and amplitude of the pressure oscillation will depend, therefore, on the type of meter being used, and on other factors, such as, for example, an amount of noise in the pressure/density measurements.

As the pressure oscillation continues, a density of the gas portion of the fluid flow, and thus the bulk density as well, also oscillates, as shown by a density signal 304. As with the pressure oscillation, the density oscillation occurs about a baseline $D_{baseline}$, and varies between a maximum amplitude $D_{MAX}$ and a minimum amplitude $D_{MIN}$. This variation in bulk density results from the pressure variation, because of the relationship between pressure and volume of a gas, as expressed by, for example, the ideal gas law of PV=nRT, where P is the pressure of a gas, V the volume occupied by the gas, and T a temperature of the gas, and further where n is the number of moles of gas present and R is the universal gas constant.

By determining the values $P_{MAX}$, $P_{MIN}$, $D_{MAX}$, and $D_{MIN}$, the gas void fraction VF may be determined, using, for example, Equation 1:

$$VF = \frac{\left[1 - \left(\frac{D_{MAX}}{D_{MIN}}\right)\right]}{\left[1 - \left(\frac{P_{MAX}}{P_{MIN}}\right)\right]} \qquad \text{Equation 1}$$

Then, the liquid density $D_{LIQ}$ may be determined, using, for example, Equation 2:

$$D_{LIQ} = \frac{D_{MAX}}{(1 - VF)} \qquad \text{Equation 2}$$

FIG. 3 illustrates the fact that the parameters ($P_{MAX}$, $D_{MAX}$) are determined with respect to a first time=$T_1$, while parameters ($P_{MIN}$, $D_{MIN}$) are determined with respect to a second time=$T_2$. As discussed below with respect to example derivations of Equations 1 and 2, other values besides ($P_{MAX}$, $D_{MAX}$) and ($P_{MIN}$, $D_{MIN}$) may be used as the pressure and density values in Equations 1 and 2.

For example, any two pressure values $P_1$ and $P_2$, and any two density values $D_1$ and $D_2$, may be used, assuming that the values $P_1$ and $D_1$ are taken at a time=$T_1$, and further assuming that the values $P_2$ and $D_2$ are taken at a time=$T_2$. In this case, the values ($P_{MAX}$, $D_{MAX}$) and ($P_{MIN}$, $D_{MIN}$) in Equations 1 and 2 would equate to the values ($P_1$, $D_1$) and ($P_2$, $D_2$), respectively.

Example(s) of full derivations for Equations 1 and 2, as well as other assumptions, requirements, or preferences that are used in such derivations, are discussed in more detail below, with respect to FIG. 5. Further, variations of Equations 1 and/or 2, and/or other equations for calculating VF and/or $D_{LIQ}$, which may not share the same assumptions, requirements, or preferences, also are discussed below. Techniques for obtaining and/or calculating the various parameters of Equations 1 and 2, and/or equivalent parameters or equations, are discussed below, with respect to FIG. 4.

Figure 4:
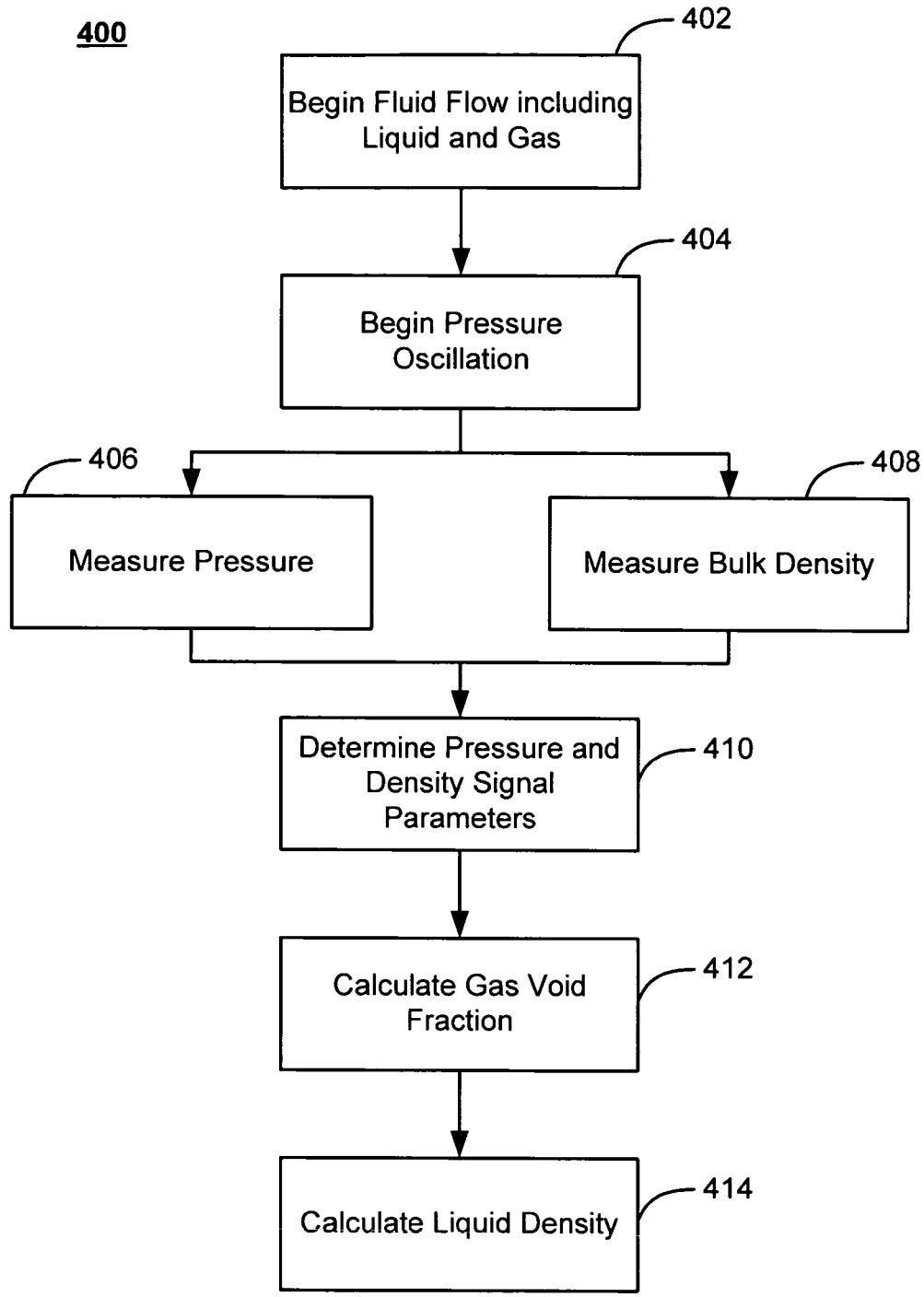
FIG. 4 is a flowchart illustrating a process for determining a liquid density of a two-phase flow.

Specifically, FIG. 4 is a flowchart 400 illustrating a process for determining a liquid density of a two-phase flow. In FIG. 4, the process begins in conjunction with a fluid flow that includes both a liquid and a gas component (402). Then, the pressure valve 230 is operated by the pressure controller 235, so as to begin a time-varying oscillation of pressure that is experienced by the fluid flow (404). The pressure oscillation is then measured (406), along with the corresponding density oscillation (408).

In the example of FIG. 3, the pressure oscillation generally takes a sinusoidal form, however, it should be understood that virtually any time-varying function may be used, or, even more generally, any function or variation that allows determination of at least $P_{MAX}$, $P_{MIN}$, $D_{MAX}$, and $D_{MIN}$, (or equivalent parameters) may be used.

Then, the pressure parameters $P_{MAX}$ and $P_{MIN}$ may be determined, and the bulk density parameters $D_{MAX}$ and $D_{MIN}$ may be determined, as well (410). Various techniques may be used to determine the parameters $P_{MAX}$, $P_{MIN}$, $D_{MAX}$, and $D_{MIN}$ (or equivalent parameters).

For example, a pressure signal at the pressure sensor 225 may be measured with an alternating current (AC) voltmeter, or current meter, in order to obtain the peak-to-peak value of the pressure signal, $P_{peak-to-peak}$. Then, the baseline value $P_{baseline}$ may be determined, using, for example, a direct current (DC) voltmeter, or current meter, to obtain what is effectively the average value or DC offset of the pressure oscillation. Once $P_{peak-to-peak}$ and $P_{baseline}$ are known, then the values $P_{MAX}$ and $P_{MIN}$ may be determined. For example, if $P_{peak-to-peak}$=2 psi, and $P_{baseline}$=1000 psi, then $P_{MAX}$=1001 psi, and $P_{MIN}$=999 psi.

Similar techniques may be used to obtain corresponding values for density parameters. As a result, all of the values $P_{MIN}$, $P_{MAX}$, $D_{MIN}$, and $D_{MAX}$ may be determined for use in Equations 1 and 2.

Selection of these values may be improved through use of the knowledge of a frequency of oscillation of the pressure and density. For example, since a frequency of oscillation is known for both the pressure and density oscillations, and if the pressure and bulk density oscillations are generally inverse to one another (neglecting any time delay between onset of the pressure oscillations and the corresponding density measurements), a selection of times=$T_1$ and $T_2$ may be made so as to correlate particular values of ($P_{MAX}$, $D_{MAX}$) and ($P_{MIN}$, $D_{MIN}$), depending on the frequency of oscillation and a response time(s) of the measuring meters that are used. As another example, a filter(s) may be selected that removes any frequencies that may be above/below the oscillation frequency, so as to improve measurements on the oscillation frequency itself.

More generally, and particularly to the extent that the oscillation frequencies are known, virtually any frequency-discriminating device(s) may be used to obtain the values ($P_{MAX}$, $D_{MAX}$) and ($P_{MIN}$, $D_{MIN}$), or equivalent values. For example, a spectrum analyzer may be used to input the pressure signal 302 and the density signal 304, and to look for activity at the oscillation frequency. Such techniques may be particularly useful, when, for example, the amplitude of the pressure signal 302 or density signal 304 is small relative to unavoidable noise present in the signal(s), which may otherwise make accurate readings from AC/DC voltmeters difficult to obtain.

As another example, the fact that the oscillation frequency is known to be caused by the operations of the valve 230 means that other techniques, such as, for example, demodulation, synchronous demodulation, and/or phase-locked loops may be used to obtain improved representation of, and calculations about, the pressure signal 302 and/or the density signal 304. For example, measurement of the pressure signal 302 may be correlated with a timing of the valve controller 235, so that measurements are only taken with respect to the pressure signal 302, and not with respect to background noise or any other signal/frequency presence.

Once the pressure and density parameters are determined, they may be used to calculate the void fraction VF, using, for example, Equation 1, above (412). Then, the VF calculation may be used to determine a liquid density $D_{LIQ}$ (414), using, for example, Equation 2. It should be apparent from Equations 1 and 2 that the liquid density $D_{LIQ}$ may be calculated directly from the values ($P_{MAX}$, $D_{MAX}$) and ($P_{MIN}$, $D_{MIN}$), or equivalent values. That is, for example, the void fraction value VF may be replaced in Equation 2 with its equivalent representation shown in Equation 1, so that an operator of a densitometer (e.g., the flowmeter 200 of FIG. 2, such as a Coriolis flowmeter) may receive a liquid density as a first or only measurement, unless the void fraction is specifically requested.

Also, although FIGS. 3 and 4 have discussed determination of VF and $D_{LIQ}$ as discrete values, it should be understood that, due to the continuous nature of the pressure signal 302 and density signal 304, a corresponding oscillation signal(s) for void fraction and/or liquid density also may be determined and displayed.

For example, if the pressure signal 302 is kept essentially constant, and more (or less) gas is introduced into the flowtube 215 (or some other variation occurs, such as, for example, introduction of a second liquid into the fluid flow), then the density signal 304 will likely change in time, and relative to the pressure signal 302. As a result, calculated values of the void fraction and liquid density will change as well, and these changing values may be calculated on an on-going basis, and displayed as oscillating signals in their own right (or just calculated periodically at desired time intervals).

Such signals may thus demonstrate a relationship between the pressure signal 302 and the density signal 304, as those signals change over time. By observing the changing values of void fraction and/or liquid density, an operator may observe effects of transient or abrupt changes in the fluid flow. As a result, for example, the operator may be able to identify or predict effects of such changes, so as to improve a future operation of an associated densitometer (e.g., a Coriolis flowmeter).

For example, if the operator determines that a particular change in void fraction or liquid density is correlated with an undesired effect, such as, for example, an inadvertent release of air into the fluid flow, then the operator may react accordingly, to correct the matter. Similarly, certain void fraction or liquid density profiles may be stored as correlating with certain undesired (or desired) events, so that appropriate action may be taken. For example, an alarm may be set to be triggered whenever the void fraction exceeds a certain amount.

Figure 5:
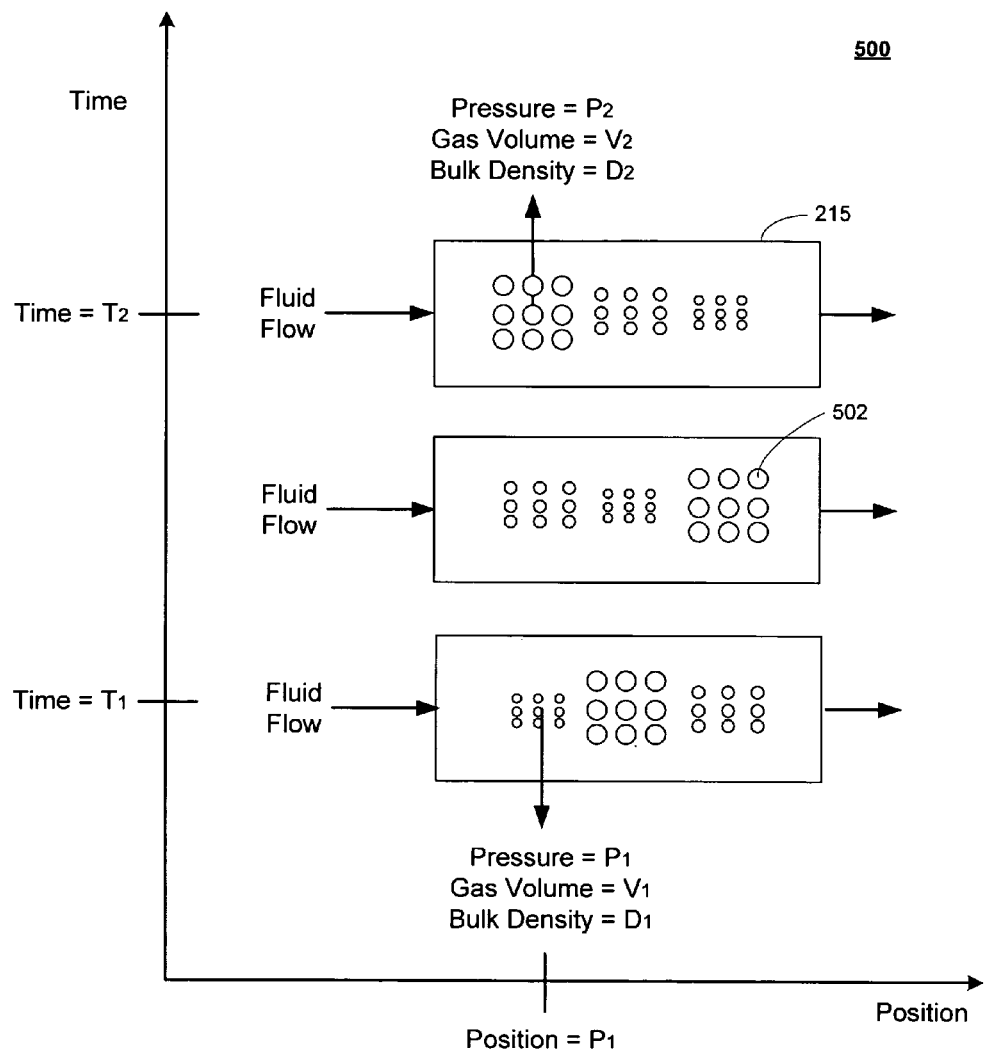
FIG. 5 is a graph illustrating effects of oscillating pressure within a portion of a flowtube, over a selected period of time.

FIG. 5 is a graph 500 illustrating effects of oscillating pressure within a portion of the flowtube 215, over a selected period of time, and is used below to help visualize the following derivations of Equations 1 and 2.

In FIG. 5, the flowtube 215 shows the effect of oscillating pressure on gas bubbles 502. Of course, it should be understood that gas within the fluid flow need not be present as bubbles, and that there are other flow regimes in which gas content may take various forms within the fluid flow. The form of the gas may depend on various factors, such as, for example, a viscosity of the liquid component, or a volume of gas within the fluid flow.

In particular, at time $T_1$ and position $P_1$, an oscillating pressure $P_1$ is at a minimum, so that a gas volume $V_{g1}$ is at a maximum, and a bulk density $D_1$ is at a minimum. As time passes from time=$T_1$ to time=$T_2$ at the position $P_1$, and the pressure signal 302 increases, the gas bubbles 502 decrease, until, at time $T_2$ and position $P_1$, an oscillating pressure $P_2$ is at a maximum, so that a gas volume $V_{g2}$ is at a minimum, and a bulk density $D_2$ is at a maximum. As shown, the position $P_1$ is maintained, so that only one density sensor and pressure sensor are required, although additional sensors may be used, as desired by an operator.

Although the pairs of values ($P_1$, $P_2$), ($V_{g1}$, $V_{g2}$), and ($D_1$, $D_2$) are discussed as maximums or minimums at the times $T_1$ and $T_2$, and as referenced above, there is no requirement that the value pairs for P, V, and D be selected and determined as such. Rather, any particular value pairs may be selected at times $T_1$ and $T_2$, respectively, so that the following derivations refer to this general case.

The following derivation(s) generally assumes that a temperature of operation is maintained at a relatively constant point, and that the gas content of the fluid flow is not absorbed within the liquid portion, and that the liquid is generally not compressible. Further, with respect to the parameter known as "phase slip," which refers to the velocities of the gas and liquid portions within the fluid flow, relative to one another, the derivation(s) assumes that there is no phase slip between the liquid and gas portions, and/or that there is no change in phase slip between the gas and liquid portions over the time period of measurement, or, at least, over the time period from time=$T_1$ to time=$T_2$. To the extent that one or more of these assumptions is not valid in a particular setting, Equations 1 and 2, and resulting values of void fraction and liquid density, may or may not be compromised to an unacceptable level. In such cases, other equations, determined without being based on the invalid assumption(s), may be used.

Under the general conditions described above, though, the ideal gas law (expressed above in the general sense), may be considered to be valid, so that the relationships hold that:

$$P_1 V_{g1} = n_1 RT$$

$$P_2 V_{g2} = n_2 RT \qquad \text{Equations 3 and 4}$$

at times=$T_1$ and $T_2$, respectively. If the moles of gas $n_1 = n_2$, then $$P_1 V_{g1} = P_2 V_{g2} \qquad \text{Equation 5}$$

so that:

$$\Delta V = V_{g1} V_{g2} = [(1/P_1) - (1/P_2)] n RT \qquad \text{Equation 6}$$

Additionally, based on the definition of density as mass/volume, quantities $M_T$ and $V_T$, referring to a total mass and volume of the fluid flow, respectively, and including the gas and liquid components, permits expression of density values as $D = M_T / V_T$ for the two volumes of gas as $D_1 = M_T/(V_{g1} + V_{liquid})$ and $D_2 = M_T/(V_{g2} + V_{liquid})$. From these equations, the above volume difference also may be expressed as:

$$\Delta V = V_{g1} - V_{g2} = M_T [(1/D_1) - (1/D_2)] \qquad \text{Equation 7}$$

Then, equating and simplifying the two expressions for this volume difference, and solving for n, provides:

$$n = \frac{P_1 P_2 M_T}{RT(P_2 - P_1)} \left[ \left( \frac{1}{D_1} \right) - \left( \frac{1}{D_2} \right) \right] \qquad \text{Equation 8}$$

This value for n allows a solution for $V_{g1}$, using the ideal gas law, so that $$V_{g1} = \frac{nRT}{P_1} = \frac{M_T\left[\left(\frac{1}{D_1}\right)-\left(\frac{1}{D_2}\right)\right]}{\left[1-\left(\frac{P_1}{P_2}\right)\right]} \quad \text{Equation 9}$$

Then, since $$V_{liquid} = V_T - V_{g1} \quad \text{Equation 10}$$

it may be determined that $$V_{liquid} = \frac{M_T}{D_1} - \frac{M_T\left[\left(\frac{1}{D_1}\right)-\left(\frac{1}{D_2}\right)\right]D_1}{\left[1-\left(\frac{P_1}{P_2}\right)\right]D_1} \quad \text{Equation 11}$$

Dividing through by $M_T$, and assuming that a mass of the gas component is negligible, relative to the mass of the liquid component, gives an inverse of the liquid density:

$$\frac{V_{liquid}}{M_T} = \frac{1}{D_1} - \left(\frac{1}{D_1}\right)\left[\frac{\left[1-\left(\frac{D_1}{D_2}\right)\right]}{\left[1-\left(\frac{P_1}{P_2}\right)\right]}\right] \quad \text{Equation 12}$$

The bracketed factor in equation 12 is equivalent to the void fraction, VF, or $$VF = \left[\frac{\left[1-\left(\frac{D_1}{D_2}\right)\right]}{\left[1-\left(\frac{P_1}{P_2}\right)\right]}\right] \quad \text{Equation 13}$$

This equivalence results from the standard, general definition of void fraction $VF=V_g/(V_g+V_{liquid})$, which, when written using the expressions for gas volume $V_g$ and liquid volume $V_{liquid}$ that are shown in Equations 9–11, reduces to the identify of Equation 13.

As a result, liquid density may be expressed as the inverse of Equation 12, so that, when simplified, the result is Equation 1:

$$\frac{M_T}{V_{liquid}} \cong D_{LIQ} = \left(\frac{D_1}{1-VF}\right) \quad \text{Equation 1}$$

where $D_1$ is $D_{MAX}$ in the particular example of FIG. 3, with respect to which Equation 1 is presented above.

Without the assumption that the mass of the gas component is negligible, an additional factor may be added to Equation 1, as shown in Equation 1a:

$$\frac{M_T}{V_{liquid}} = D_{LIQ} = \left(\frac{D_1}{1-VF}\right)\left(1-\frac{VF*D_{g1}}{D_1}\right) \quad \text{Equation 1a}$$

where the density of the gas component at time=$T_1$ (i.e, the value $D_{g1}$ in Equation 1A) may be determined from the ideal gas law, if the type of gas is known (e.g., air). Other variations on Equation 1, or other equations entirely, may be used to determine $D_{LIQ}$ and/or VF, depending on, for example, the types of fluids being measured, or the type of densitometer being used.

The above discussion is generally provided in the example of the context of the digital flowmeter of FIG. 2. However, it should be understood that any vibrating or oscillating densitometer or flowmeter, analog or digital, that is capable of measuring multi-phase flow that includes a gas phase of a certain percentage may be used.

Based on the above, it is possible to determine liquid densities of a multi-phase flow including a gas in a wide variety of applications. For example, a process fluid that includes oil, water, and air may be accurately measured to determine relative densities and percentages of the oil and water. Similar determinations may be made in many other applications, including, for example, many chemical and/or food measurement processes.

A number of implementations have been described. Nevertheless, it will be understood that various modifications may be made. Accordingly, other implementations are within the scope of the following claims.

What is claimed is:

1. A method comprising:
   oscillating a pressure of a process fluid in a flowtube according to a periodic function of known frequency, the process fluid containing a liquid component and a gas component;
   determining pressure values and density values of the process fluid that occur during the oscillation of the pressure; and
   determining a liquid density of the liquid component, based on the pressure values and the density values.

2. The method of claim 1 further comprising determining a percentage of the gas component, by volume, within the process fluid and during the oscillation of the pressure, based on the pressure values and the density values.

3. The method of claim 1 wherein determining the pressure values and the density values comprises:
   determining a first pressure value and a second pressure value of the process fluid at a first time and a second time, respectively, during the oscillation of the pressure;
   determining a first density value and a second density value of the process fluid at the first time and the second time, respectively.

4. The method of claim 3 wherein determining the liquid density comprises calculating the liquid density using an equation:

$$D_{LIQ} = \frac{D_1}{\left(1-\left[\frac{\left[1-\left(\frac{D_1}{D_2}\right)\right]}{\left[1-\left(\frac{P_1}{P_2}\right)\right]}\right]\right)}$$

where $D_{LIQ}$ is the liquid density, $D_1$ and $D_2$ are the first density value and the second density value, respectively, and $P_1$ and $P_2$ and are the first pressure value and the second pressure value, respectively.

5. The method of claim 3 further comprising determining a percentage of the gas component, by volume, within the process fluid and during the oscillation of the pressure, based on the pressure values and the density values, using an equation:

$$VF = \frac{\left[1 - \left(\frac{D_1}{D_2}\right)\right]}{\left[1 - \left(\frac{P_1}{P_2}\right)\right]}$$

where VF is the percentage of the gas component, by volume, $D_1$ and $D_2$ are the first density value and the second density value, respectively, and $P_1$ and $P_2$ and are the first pressure value and the second pressure value, respectively.

6. The method of claim 1 wherein determining the pressure values comprises receiving a signal representing the oscillating pressure of the process fluid and filtering the signal to remove at least some frequencies other than the known frequency.

7. The method of claim 1 wherein determining the density values includes measuring the density of the process fluid using a Coriolis flowmeter.

8. The method of claim 1 wherein oscillating the pressure of the process fluid comprises operating a pressure valve to establish the oscillation of the pressure according to the periodic function of known frequency, such that the pressure values and the density values oscillate in accordance with the periodic function.

9. The method of claim 8 wherein determining the pressure values and the density values comprises:
determining amplitudes of oscillation of the pressure values and the density values;
determining average values of the pressure values and the density values; and
determining the pressure values and the density values, based on the amplitudes of oscillation and the average values.

10. The method of claim 1 wherein determining the pressure values comprises receiving a signal representing the oscillating pressure of the process fluid and detecting activity of the signal at the known frequency.

11. The method of claim 1 wherein the known frequency is small compared to a vibration frequency of the flowtube, such that the known frequency substantially does not affect operating measurements of the flowtube.

12. The method of claim 1 wherein determining the pressure values and the density values comprises determining the pressure values and the density values with respect to a single portion of the flowtube.

13. A system comprising:
a pressure controller operable to oscillate a pressure of a fluid within a flowtube in accordance with a periodic function of known frequency, the fluid including a gas component and a liquid component;
a pressure sensor operable to determine pressure values associated with the fluid that occur during the oscillation of the pressure;
a densitometer that is operable to determine density values associated with the fluid that occur during the oscillation of the pressure; and
a liquid density determination system that is operable to determine a liquid density of the liquid component of the fluid, based on the pressure values and the density values.

14. The system of claim 13 comprising a void fraction determination system that is operable to determine a percentage of the gas component, by volume, within the fluid and during the oscillation of the pressure, based on the pressure values and the density values.

15. The system of claim 13 wherein:
the pressure sensor is operable to determine the pressure values by determining a first pressure value and a second pressure value of the fluid at a first time and a second time, respectively, during the oscillation of the pressure, and wherein
the densitometer is operable to determine a first density value and a second density value of the fluid at the first time and the second time, respectively.

16. The system of claim 13 wherein the pressure controller is operable to oscillate the pressure of the fluid by operating a pressure valve to oscillate the pressure according to the periodic function of known frequency.

17. A densitometer controller comprising:
a pressure controller operable to oscillate a pressure of a fluid within a flowtube in accordance with a periodic function of known frequency, the fluid including a gas component and a liquid component;
a pressure determination system operable to determine pressure values associated with the fluid that occur during the oscillation of the pressure;
a density determination system operable to determine density values associated with the fluid that occur during the oscillation of the pressure; and
a liquid density determination system that is operable to determine a liquid density of the liquid component of the fluid, based on the pressure values and the density values.

18. The densitometer controller of claim 17 comprising a void fraction determination system that is operable to determine a percentage of the gas component, by volume, within the fluid and during the oscillation of the pressure, based on the pressure values and the density values.

19. The densitometer controller of claim 17 wherein:
the pressure determination system is operable to determine the pressure values by determining a first pressure value and a second pressure value of the fluid at a first time and a second time, respectively, during the oscillation of the pressure, and
the density determination system is operable to determine a first density value and a second density value of the fluid at the first time and the second time, respectively.

20. The densitometer controller of claim 17 wherein the pressure controller is operable to oscillate the pressure of the fluid by operating a pressure valve to establish an oscillation of the pressure according to the periodic function of known frequency.

* * * * *